(12) United States Patent
Zellner et al.

(10) Patent No.: US 9,927,429 B2
(45) Date of Patent: Mar. 27, 2018

(54) TROPOMYOSIN ISOFORMS RELATED TO ALZHEIMERS DISEASE AND MILD COGNITIVE IMPAIRMENT

(71) Applicant: Randox Laboratories Ltd., Antrim (GB)

(72) Inventors: Maria Zellner, Vienna (AT); Ellen Umlauf, Vienna (AT)

(73) Assignee: RANDOX LABORATORIES LTD., Northern Ireland (GB)

( * ) Notice: Subject to any disclaimer, the term of this patent is extended or adjusted under 35 U.S.C. 154(b) by 0 days.

(21) Appl. No.: 14/411,496

(22) PCT Filed: Jul. 8, 2013

(86) PCT No.: PCT/EP2013/064397
§ 371 (c)(1),
(2) Date: Dec. 27, 2014

(87) PCT Pub. No.: WO2014/006224
PCT Pub. Date: Jan. 9, 2014

(65) Prior Publication Data
US 2015/0198590 A1    Jul. 16, 2015

(30) Foreign Application Priority Data
Jul. 6, 2012 (GB) .................... 1212084.6

(51) Int. Cl.
*G01N 33/53* (2006.01)
*G01N 33/566* (2006.01)
*C07K 16/00* (2006.01)
*G01N 33/68* (2006.01)

(52) U.S. Cl.
CPC ..... *G01N 33/5308* (2013.01); *G01N 33/6896* (2013.01); *G01N 2333/4712* (2013.01); *G01N 2800/2814* (2013.01); *G01N 2800/2821* (2013.01)

(58) Field of Classification Search
None
See application file for complete search history.

(56) References Cited

U.S. PATENT DOCUMENTS 9,285,374 B2 *   3/2016   Umlauf ............... C07K 14/47
2008/0318229 A1  12/2008  Zellner et al.

FOREIGN PATENT DOCUMENTS

EP    1 847 615 A1    10/2007
WO    2011/067610 A1   6/2011

OTHER PUBLICATIONS

Lindberg, Pia, International Search Report, PCT/EP2013/064397, dated Sep. 9, 2013.
Schevzov et al., "Tissue-specific Tropomyosin Isoform Composition," J. of Histochem. & Cytochem., vol. 53, No. 5, pp. 557-570, May 1, 2005.

* cited by examiner

*Primary Examiner* — Olga N Chernyshev
(74) *Attorney, Agent, or Firm* — Gavrilovich, Dodd & Lindsey LLP

(57) ABSTRACT

The present invention provides an in vitro method to aid the diagnosis of Alzheimer's disease (AD) or Mild Cognitive Impairment (MCI), comprising determining the level of expression of one or more tropomyosin isoform(s) corresponding to P09493-3 and/or P09493-1 in a patient's sample. A kit comprising probes that bind to tropomyosin isoforms P09493-3 and P09493-1 is also provided.

7 Claims, 3 Drawing Sheets

Silver Stain of 2D-gel

Western Blot of 1D (left) and 2D gel (right)

Reference Blot

US 9,927,429 B2

TROPOMYOSIN ISOFORMS RELATED TO ALZHEIMERS DISEASE AND MILD COGNITIVE IMPAIRMENT

CROSS REFERENCE TO RELATED APPLICATIONS

This application is a U.S. National Stage Application filed under 35 U.S.C. § 371 and claims priority to International Application No. PCT/EP2013/064397, filed Jul. 8, 2013, which application claims priority to Great Britain Application No. 1212084.6, filed Jul. 6, 2012, the disclosure of which are incorporated herein by reference in their entirety.

BACKGROUND OF THE INVENTION

Due to increasing longevity, dementia-based illness is becoming the main global health-related burden of medical budgets and is a recognised stressor of carers/families of the affected. Alzheimer's disease (AD) represents the most prevalent neurodegenerative pathology and the identification of therapeutic and improved diagnostic methods for patient treatment and screening are constantly being sought. Although psychometric tests such as the mini-mental state exam are generally good predictors of AD, post-mortem examination remains the only unequivocal method of Alzheimer's diagnosis. Loss of memory is a common phenomenon amongst the aged. In the event where severe memory loss is the predominant symptom this condition is termed mild cognitive impairment (MCI) and is often seen as a very early stage of AD. At this stage treatment may be more efficacious than later on. The conversion rate of patients with MCI to clinical AD is described to be 50% within 3 years (Karas et al 2008). The use of protein biomarkers in diagnostic medicine is increasing. Identification of protein biomarkers of AD, especially those present in readily accessible biological fluids such as blood and urine, represents a desirable and effective alternative to current diagnostic methods. Tropomyosin is a fibrous molecule that consists of two α-helices. It is widely distributed in all cell types, where it regulates the shortening of the muscle filaments actin and myosin. In mammals, differential splicing of four highly conserved genes can give rise to more than 40 isoforms (Schevzov et al. 2005). Furthermore, each isoform can be subject to various degrees of post-translational modification, including phosphorylation and glycosylation. Two of the most common analytical techniques used in protein separation and identification are two dimensional gel electrophoresis (2-D DIGE) and 2D Western blot. EP2293075, using 2-D DIGE to identify possible biomarkers of AD in platelet samples, highlighted two tropomyosin isoforms assigned to the Swissprot/Uniprot Accession Number P07951 and NCBI/Genbank accession numbers BAB14554/AK023385.

SUMMARY OF THE INVENTION

The present invention provides methods and kits for the detection of MCI and AD-related tropomyosin isoforms incorporating exon 1a, and optionally exon 9d.

According to a first aspect, the invention provides an in vitro method to aid the diagnosis of Alzheimer's disease (AD) or Mild Cognitive Impairment (MCI), comprising determining the level of expression of one or more tropomyosin isoform(s) corresponding to P09493-3 and/or P09493-1 in a patient's sample.

According to a second aspect, the invention provides a kit comprising probes that bind to tropomyosin isoforms P09493-3 and P09493-1, characterised by a first probe that binds to a common epitope of P09493-3 and P09493-1 that does not comprise exon 1a and a second probe that binds specifically to exon 1a.

According to a third aspect, the invention provides an agent that alters the concentration levels of one or more tropomyosin isoform(s) P09493-3 and P09493-1, for use in treating AD or MCI.

DESCRIPTION OF THE FIGURES

FIG. 2 shows a 2D Western Blot evaluation of an antibody to exon 1a; and

DETAILED DESCRIPTION OF THE INVENTION

Unless otherwise specified, references to exons 1a and 9d refer to the amino acid sequences shown below:

```
Exon 1a:
                                          (SEQ ID NO. 1)
-Leu-Asp-Lys-Glu-Asn-Ala-Leu-Asp-Arg-Ala-Glu-Gln- Ala-Glu-Ala-Asp-Lys-Lys-Ala-Ala- Exon 9d:
                                          (SEQ ID NO. 2)
-Glu-Lys-Val-Ala-His-Ala-Lys-Glu-Glu-Asn-Leu-Ser- Met-His-Gln-Met-Leu-Asp-Gln-Thr-Leu-Leu-Glu-Leu- Asn-Asn-Met-
```

The terms "patient" and "subject" are used interchangeably herein and refer to any animal (e.g. mammal), including, but not limited to, humans, non-human primates, canines, felines, rodents and the like, which is to be the recipient of the diagnosis. Preferably, the subject or patient is a human. The terms "drug" and "agent" are used interchangeably herein, and refer to a chemical or biological substance that exerts an effect on a biological system.

Figure 2:
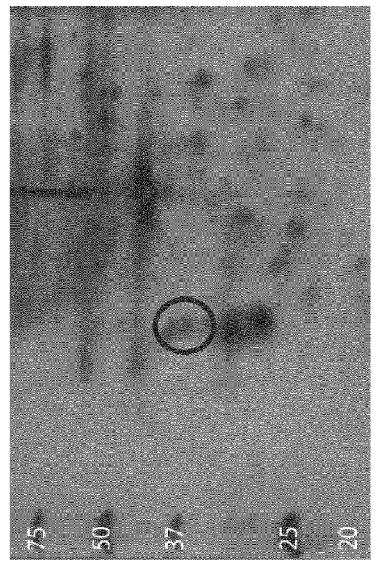
Figure 2:
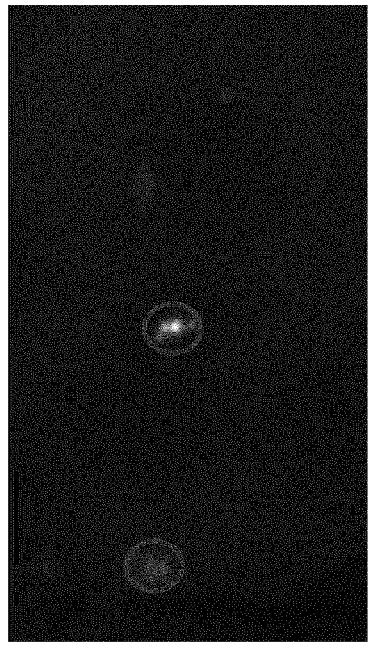
Figure 2:
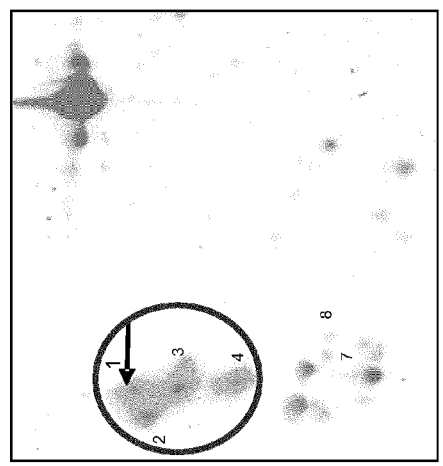
Figure 3:
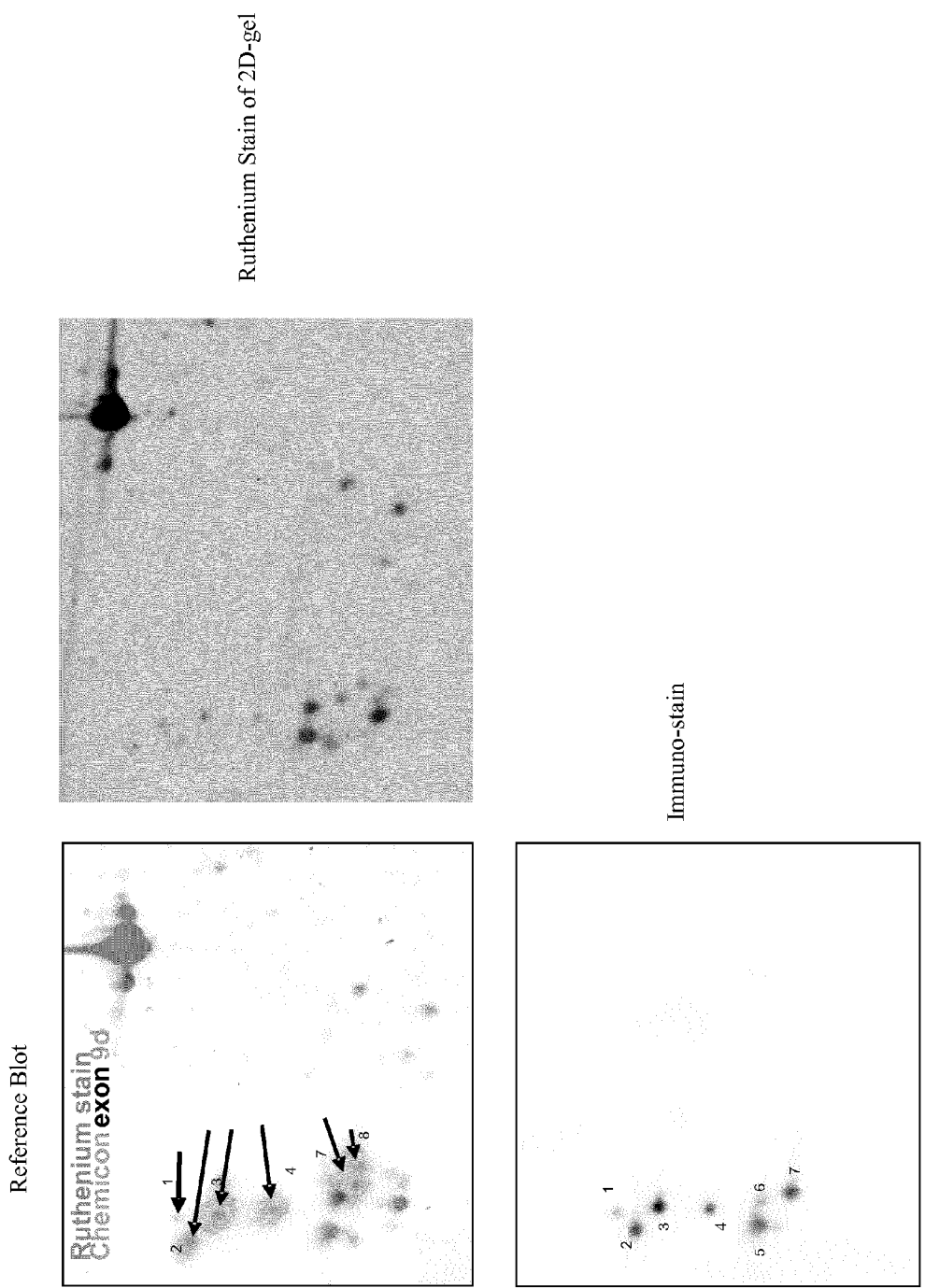
FIG. 3 shows a 2D Western Blot evaluation of an antibody to exon 9d.

As used herein, the term "tropomyosin isoforms" includes all tropomyosin-based proteins including those derived from differential genetic splicing and post-translational modified forms. The three tropomyosin isoforms corresponding to Spots 2, 3 and 4 of FIGS. 1, 2, and 3 have been assigned to UniprotKB (UNiprotKB; world wide web at uniprot.org/uniprot) accession number P09493-3 based on 2D-WB and mass spectrometry data; reference to P09493-3 herein, therefore, implies Spots 2, 3 and 4 unless otherwise stated. Reference to P09493 as described herein implies P09493-3 (Spots 2, 3, and 4) and P09493-1 ; reference to P09493-1 herein is as described in Uniprot KB and corresponds to Spot 1.

According to a first aspect, the invention provides a method to aid in the diagnosis of Mild Cognitive Impairment (MCI) and/or Alzheimer's disease (AD), comprising detecting and measuring in an in vitro patient sample the level of expression of one or more of P09493 and/or their post-translational analogues. In a preferred embodiment, the tropomyosin isoforms to be detected and measured correspond to one or more of P09493-3 (Spots 2, 3 and 4). As used herein 'level of expression' or 'expression level' refers to the amount of specified protein or mRNA coding for the protein. P09493 can be used with other biomarkers of MCI and AD to improve the diagnostic power of a test for AD or MCI. Protein biomarkers are not used in isolation and the skilled person will recognize that in using P09493 in the diagnosis of MCI or AD, diagnosis will also involve the clinical assessment of the patient, using physical and cognitive tests such as the MMSE, to aid in the categorization of the patient as AD or MCI. Depending on the diagnostic power of the biomarkers used in conjunction with P09493 (assessed for example, by ROC curve analysis and sensitivity and specificity), it is possible that a biochemical biomarker test might be the principal diagnostic tool used to diagnose AD or MCI. The tropomyosin isoforms to be detected contain exon 1a and optionally exon 9d; tropomyosin isoforms P09493-3 comprise exons 1a and 9d, while tropomyosin isoform P09493-1 incorporates exon 1a but not exon 9d. The tropomyosin isoforms to be detected and measured are preferably derived from platelets from a patient's blood sample. In MCI and AD patients, it has been shown that the P09493 shows a significant increase in concentration compared to a control value.

Preferably, the control value is the concentration of P09493 derived from a sample, preferably a platelet sample, obtained from a healthy subject. Alternatively, the control may be a reference value. The platelets to be measured in prospective AD patients and healthy controls are preferably derived using the method described in EP1891445 which describes a method that results in the extraction of non-activated platelets from a blood sample. The control data can also be values from samples taken from the MCI/AD patients themselves prior to onset of MCI/AD. It is common practice in such biomarker diagnostic methods to utilise a control data set that has been previously derived and archived. In a preferred embodiment, an increase in the level of expression of the one or more tropomyosin isoforms compared to a control value is indicative of AD or MCI. The method of the invention may optionally further comprise treating a patient how has been diagnosed as having AD or MCI (or whom the method of the invention indicates is likely to have AD or MCI) with an agent that alters the concentration levels of P09493.

In a second aspect, the invention provides a kit comprising a first probe that specifically recognises exon 1a and a second probe that specifically recognises a common epitope of P09493-3 and P09493-1 that does not comprise exon 1a for use in MCI and AD diagnosis. For the purposes of diagnosis of AD or MCI, the second probe can be specific to exon 9d. Specifically implies that within the detection range of the test the probes substantially detect only P09493 i.e. any binding by the probes of proteins other than P09493 is at such a low level that it does not affect the integrity of the diagnostic result. The probes are preferably antibodies.

As used herein, the term "antibody" refers to an immunoglobulin which specifically recognises an epitope on a target as determined by the binding characteristics of the immunoglobulin variable domains of the heavy and light chains ($V_H$S and $V_L$S), more specifically the complementarity-determining regions (CDRs). Many potential antibody forms are known in the art, which may include, but are not limited to, a plurality of intact monoclonal antibodies or polyclonal mixtures comprising intact monoclonal antibodies, antibody fragments (for example $F_{ab}$, $F_{ab}$', and $F_r$ fragments, linear antibodies single chain antibodies and multi-specific antibodies comprising antibody fragments), single chain variable fragments (scF$_v$S), multi-specific antibodies, chimeric antibodies, humanised antibodies and fusion proteins comprising the domains necessary for the recognition of a given epitope on a target. Preferably, references to antibodies in the context of the present invention refer to monoclonal antibodies. Antibodies may also be conjugated to various reporter moieties for a diagnostic effect, including but not limited to radionuclides, fluorophores or dyes. Reference to antibodies also includes short chain variable fragments and other sub-structural variants of 'whole' antibodies. It will be recognised by the skilled person that for antibodies to have application in the methods and kits of the invention they are required to recognise exons 1a and optionally 9d. Such recognition could involve each exon-specific antibody recognising the full exon amino acid sequence or a sub-set of the exon sequence. For example, a sub-set of exon 1a recognised by the antibody might only comprise 7 amino acids, but still be specific to exon 1a. Other probes suitable for use in the invention are molecules capable of recognising P09493 such as aptamers, molecular imprinted polymers etc.

A third aspect of the invention is directed to the use of an agent that alters the concentration levels of P09493; such a use is intended as therapy to alleviate or suppress the symptoms of MCI and AD.

The invention also provide a method of treating MCI and/or AD, comprising (i) determining whether the level of expression of one or more tropomyosin isoform(s) corresponding to P09493-3 and/or P09493-1 in a patient's sample is increased compared to a control; and (ii) administering an agent that alters the concentration levels of P09493.

The content of all publications referred to herein is incorporated by reference.

The invention is described with reference to the accompanying drawings, by the following non-limiting examples.

EXAMPLES

Methods
Study Population
Alzheimer Patients: Forty seven AD patients were enrolled in the study. The neuropsychological test battery of CERAD (Consortium to Establish a Registry for Alzheimer's Disease was performed on the day of blood sampling. None of the patients had been treated with AD-related medication e.g. acetylcholinesterase inhibitors of memantine. Moreover, dementia patients did not receive consistent chronic antipsychotic drug treatments which may have influenced Mao-B expression. To exclude other cause of cognitive impairment (e.g., stroke or tumour) all patients underwent structural imaging scanning of the brain (magnetic resonance imaging) except for two patients that underwent computed tomography (claustrophobia, metal implant) instead. Based on the CERAD criteria (Hypertext Transfer Protocol at cerad.mc, duke, edu/Assement.htm/) e.g.: clinical history, brain imaging and neuropsychological CERAD test battery the following diagnoses were made: 47 AD (9 autopsy-confirmed). A neuropathological post mortem examination was performed in a total of 13 patients. Patients died ten to 18 months after the blood sampling. In nine of 47 patients with clinically suspected AD the clinical diagnosis was neuropathologically confirmed and four of 13vascular dementia (VD) cases fulfilled neuropathological criteria for mixed type dementia (AD and VD). Neuropathological examination followed a standard protocol including Haematoxylin/Eosin staining, modified Bielschowsky impregnation, and immunohistochemistry for tau protein (antibody AT-8, Innogenetics, Ghent, Belgium), β-amyloid (clone 4G8, Signet Labs, Dedham, MA) and α-synuclein (mono- and polyclonal antibodies, Chemicon, Temecula, Calif.). Neuropathological diagnoses were made according to established postmortem consensus criteria, for AD including CERAD scores. AD cases showed neuropathology indicative for CERAD C and Braak stages V/VI thereby fulfilling high likelihood for AD according to NIA-Reagan Institute "dementia" criteria. Controls: The age- and sex matched control group for AD of 49 subjects) with no signs of neurodegenerative diseases or cognitive impairment. All subjects were interviewed and neuropsychological examination (MMSE) was made by an experienced psychologists. All individuals included in our study were non-smokers. Mild Cognitive Impairment was defined according to Petersen et al (1999 & 2004).

Ethical Aspects of the Study Design

The protocol was approved by the local ethics commission and the study was carried out in accordance with the principles of the Declaration of Helsinki as revised in 2000. Informed consent was obtained from each subject or from a solicitor, after the purpose and procedure of the study had been explained.

Sample Preparation

Blood was drawn without stasis from the antecubital vein into vacuum tubes (Greiner Bio-One GmbH, Kremsmünster, Austria) containing 0.129 mol/L sodium citrate as anticoagulant (mixing ratio 1:9 with blood). The first tube drawn was discarded to avoid any tissue contamination from venepuncture. A differential haemogram was made on a MicroDiff 18 Blood Analyser (Coulter Electronics, Miami, Fla., USA). Platelet isolation procedure and protein precipitation were carried out as previously described [31]. Briefly, the pellet was resolubilised in denaturing 2-D sample buffer containing 7 M urea, 2 M thiourea, 4% CHAPS, 20 mM Tris-HCl (pH 8.5) by shaking overnight at 4° C. Seventy microliters of the sample buffer was used per 100×106 platelets. The protein concentration in resolubilised samples was determined in triplicate using a Coomassie brilliant blue protein assay kit with BSA as the standard protein (Pierce Biotechnology, Rockford, Ill., USA). With appropriate dilution, the 2-D sample buffer components do not interfere with the protein assay. Therefore, the samples were diluted 1:20 with PBS and 5% of the 2-D sample buffer was added in the BSA standards. The internal standard for 2D DIGE analysis was composed by pooling the same amount of total protein of each study sample. Aliquots of internal standard and study individual samples were stored at −80° C. Protein labelling with fluorescent cyanine dyes (CyDyes, GE Healthcare, Uppsala, Sweden) was carried out prior to electrophoresis according to the manufacturer's instructions with minor modifications. The ratio of CyDye to protein was reduced to 5 pmol of dye per µg of protein. The internal standard was labelled with Cy2, and the samples were labelled alternately with Cy3 or Cy5. For Real Time quantitative Reverse Transcription PCR (qRT-PCR) total RNA was extracted from gel-filtrated platelets as described before .

2D DIGE Electrophoresis and Gel Image Analysis

Electrophoresis and gel image processing were performed as previously described. Briefly, 24 cm pH 4-7 9 IPG-Drystrips were passively rehydrated in a modified rehydration solution (7M urea, 2M thiourea, 4% CHAPS, 70 mM DTT and 0.5% ampholytes pH 4-7) containing the dye labelled sample. Afterwards 25 µg per dye labelled protein were applied via passive rehydration. Isoelectric focusing was carried out until 30 kVh were reached. In the second dimension 11.5% SDS-PAGE (35 V for 1 h, 50 V for 1.5 h and finally 110 V for 16.5 h at 10° C.) was performed and gels were scanned at a resolution of 100 µm using a Typhoon 9410 imager (GE Healthcare, Uppsala, Sweden). Spot detection was performed on the gel images using the DeCyder software module Differential In-gel Analysis (version 6.00.28; GE Healthcare, Uppsala, Sweden) setting the target spot number to 2500. Each gel was added to the appropriate workspace and group and matched against the master gel using the DeCyder module Biological Variation Analysis (version 6.01.02). Gel image analysis procedure was described more in detail previously.

Protein Identification

Proteins were identified by mass spectrometric analysis. Preparation of tryptic protein hydrolysates for the latter was carried out as previously described. Peptides were loaded on a Zorbax 300SB-C8(5 µm, 0.3 mm×5 mm) column and separated by nanoflow liquid chromatography (1100 Series LC system, Agilent, Palo Alto, Calif.) with a Zorbax 300SB-C18 (5 µm, 75 µm×150 mm) column at a flow-rate of 250 nl/min using a gradient from 0.2% formic acid and 3% acetonitrile to 0.2% formic acid and 45% acetonitrile over 12 minutes. Peptide identification was accomplished by tandem mass spectrometry (MS/MS) fragmentation analysis with an iontrap mass spectrometer (XCT-Plus, Agilent) equipped with an orthogonal nanospray ion source. The MS/MS data were interpreted by the Spectrum Mill MS Proteomics Workbench software (Version A.03.03, Agilent) and searched against the SwissProt database for human proteins (version 14.3 containing 20,328 entries) allowing for a precursor mass deviation of 1.5 Da, a product mass tolerance of 0.7 Da and a minimum matched peak intensity (% SPI) of 70% and one missed cleavage. Due to previous chemical modification, carbamidomethylation of cysteines was set as fixed modification. The false discovery rate for peptides scoring higher than 13 is consistently less than 1%, resulting in a certainty better than 99.9% for proteins identified with two or more peptides scoring higher than 13.

Antibody Production

Sheep were immunised on a monthly basis with peptide sequences corresponding to H-Cys-Leu-Asp-Lys-Glu-Asn-Ala-Leu-Asp-Arg-Ala-Glu-Gln-Ala-Glu-Ala-Asp-Lys-Lys-Ala-Ala-NH2 (SEQ ID NO. 3) and H-Cys-Glu-Lys-Val-Ala-His-Ala-Lys-Glu-Glu-Asn-Leu-Ser-Met-His-Gln-Met-Leu-Asp-Gln-Thr-Leu-Leu-Glu-Leu-Asn-Asn-Met-OH (SEQ ID NO. 4) conjugated to bovine serum albumin (BSA) via N-terminal cysteine residues. The resulting immunogens were administered to adult sheep on a monthly basis in order to generate a polyclonal response. Lymphocytes were then harvested and fused with heteromyeloma cells. Supernatants from the resulting hybridomas were screened for the presence of exon specific antibodies, employing ELISA based assays, in which the microtiter plates were coated with full length protein. Positive hybridomas were cloned to stability. Antibodies generated by the resulting monoclonal hybridomas were purified, characterised by 1 and 2 dimensional western blotting (1D and 2D WB) and employed in the development of a biochip sandwich immunoassay. The assay was applied to the Evidence Investigator analyser which utilises biochip array technology based on ELISA immunoassay principles (Fitzgerald et al 2005).

Two Dimensional Western Blot Analysis

For 2D Western Blot analysis 30 µg of TCA-precipitated and urea/thiourea/CHAPS-resolubilised platelet proteins were separated in the first dimension by IEF on a 24 cm pH 4-7 IPG strip (GE Healthcare). The second dimension was done by SDS PAGE on a 13×16 cm gel and the separated proteins were transferred to a nitrocellulose membrane (Pall, East Hills, N.Y.). Total protein on the membrane was stained using a ruthenium-(II)-tris-(bathophenanthroline disulfonate) (RuBPS) based fluorescence dye. Afterwards, the membrane was blocked with 5% non-fat dry milk in PBS containing 0.3% Tween-20 (PBS-T) for 2 hours. AD-related tropomyosin isoforms were detected by incubating the membrane: a) for anti-1a exon detection, HRP-labelled anti-1a exon antibody (1/1000), incubation for 1 h, detection with Luminol PLUS/Peroxide, exposure 10 sec b) for anti-9d exon detection, HRP-labelled anti-9d exon antibody (1/1000), incubation for 1 h, detection with Luminol PLUS/Peroxide, exposure 30 sec-1 min.

Results

Figure 1:
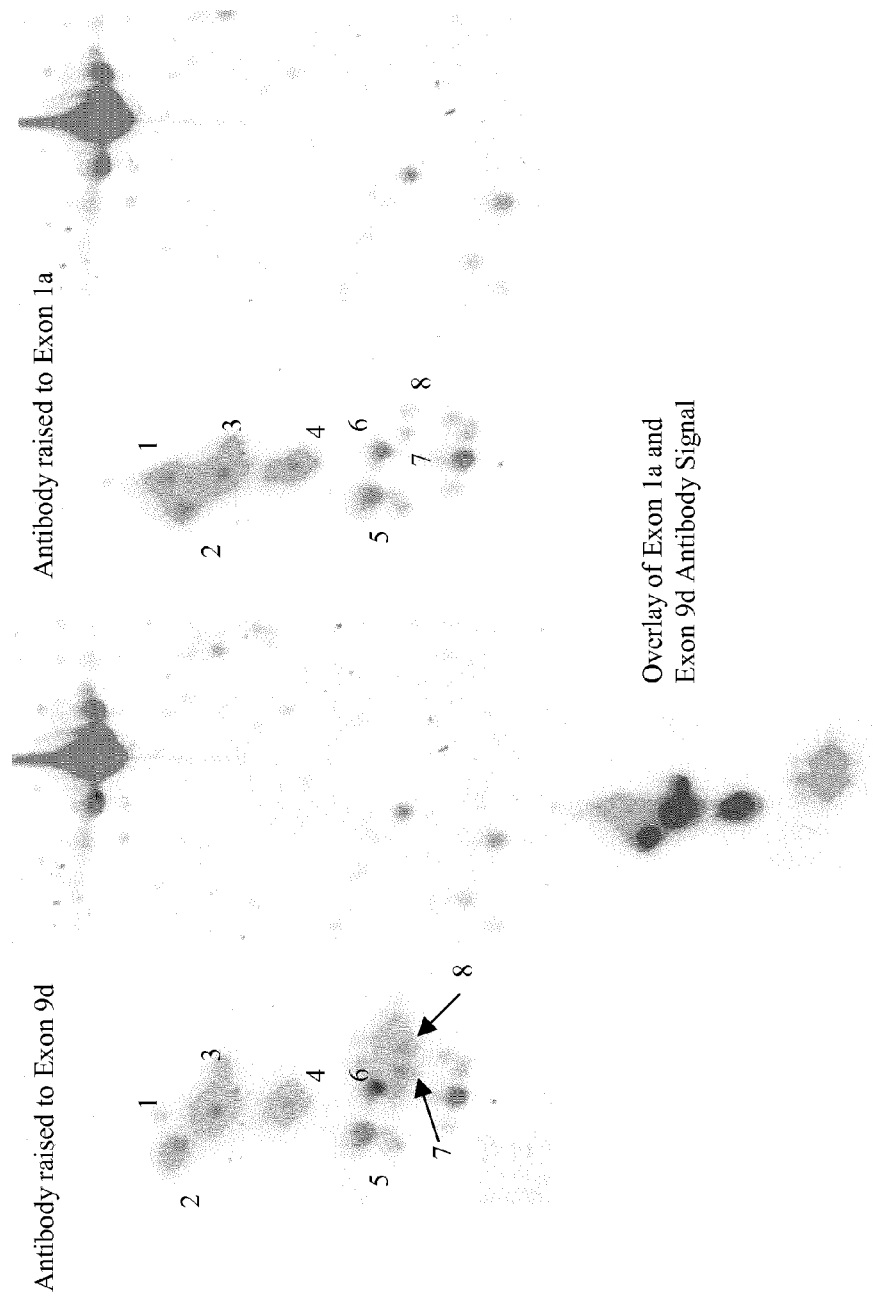
FIG. 1 shows ruthenium stains of antibodies raised to exons 1a and 9d.

An exon 9d specific capture antibody was selected for immobilisation on the surface of the biochip and an exon 1a specific detector antibody was conjugated to horseradish peroxidase to generate the assay tracer. The biochip immunoassay developed employing these immunoreagents exhibited specificity for three of the four AD and MCI related P09493 tropomyosin isoforms. 1D and 2D Western Blot confirmed that the antibodies generated to exons 1a and 9d, bound to spots 2, 3 and 4(FIG. 1). It was also found that each of the upregulated tropomyosin isoforms in AD and MCI samples incorporated exon 1a. The four other tropomyosin isoforms assigned by mass-spectrometry, corresponding to spots 5, 6, 7 and 8 (FIG. 1), none of which incorporated exon 1a, were not upregulated in AD and MCI samples. Assay sensitivity was <10 ng/ml (measuring range 0-700 ng/ml) and within-run precision was <10% for standard level concentrations. Under the applied experimental conditions Spot 1 had a pI=4.5 and a MW=~37 kDa, Spot 2 had a pI=4.5 and a MW=~37 kDa Spot 3 had a pI=4.6 and a MW=~35 kDa and Spot 4 had a pI=4.56 and a MW=~33 kDa. In isolated blood platelets, levels of up to 12 µg/ml were detected. Table 1 (the % change rows) confirms that the P09493 tropomyosin isoforms corresponding to spots 1, 2, 3 and 4, alone and in combination, are all upregulated in AD and MCI patients compared to control. t-Tests highlight that Spot 2 and a combination of all four spots are significantly upregulated in AD and MCI patients compared to control (P<0.05). The results of this study indicate that the detection and measurement in an in vitro sample of a patient suspected of having AD or MCI of upregulated P09493-3 and P09493-1 tropomyosin isoforms is predictive of AD and MCI.

References

Karas et al (2008). *Am. J. Neuroradiol.*, 29(5): 944-949
Schevzov G. et al (2005). *J. Histochem. Cytochem.*, 53(5):557-570
Fitzgerald et al. (2005). *Clin. Chem.*, 51(7): 1165-1176
Petersen et al (1999). *Arch. Neurol.*, 56(3): 303-308
Petersen et al (2004). *J. Intern. Med.* 256(3): 183-194.

TABLE 1

2-Sided T-test of Relative mean concentrations of tropomyosin isoforms in AD, MCI and Controls (Standard deviation in brackets)

| Exon(s) | 1a | 1a and 9d | 1a and 9d | 1a and 9d | 9d | | | 1a/1a + 9d | 1a + 9d |
|---|---|---|---|---|---|---|---|---|---|
| Tropomyosin isoform | 1 P09493-1 | 2 P09493-3 | 3 P09493-3 | 4 P09493-3 | 5 P67936 | 7 P09493-2 | 6 P06753 | P09493-1&3 | only P09493-3 |
| AD | 1.07 (0.35) | 1.1 (0.40) | 0.93 (0.25) | 1.02 (0.33) | 1.03 (0.11) | 0.98 (0.16) | 1.03 (0.13) | 4.1 (1.10) | 3.01 (0.87) |
| AD Control | 0.88 (0.26) | 0.79 (0.28) | 0.8 (0.29) | 0.89 (0.20) | 1.01 (0.11) | 0.96 (0.17) | 1 (0.10) | 3.34 (0.82) | 2.45 (0.67) |
| % change AD | 121 | 139 | 118 | 115 | 102 | 103 | 102 | 123 | 123 |
| t-Test 2-sided AD | 0.03104 | 0.00008 | 0.00952 | 0.04883 | 0.68447 | 0.68293 | 0.36702 | 0.00043 | 0.00037 |
| MCI | 1.11 (0.32) | 1.15 (0.44) | 0.92 (0.36) | 0.99 (0.30) | | | | 4.17 (1.03) | 3.06 (0.81) |
| MCI Control | 0.97 (0.13) | 0.87 (0.39) | 0.77 (0.27) | 0.89 (0.29) | | | | 3.48 (0.95) | 2.5 (0.96) |
| % change MCI | 114 | 132 | 119 | 111 | | | | 120 | 122 |
| t-Test 2-sided MCI | 0.036 | 0.035 | 0.113 | 0.404 | | | | 0.019 | 0.048 |

The invention claimed is:

1. A method to determine the expression level of one or both tropomyosin isoform(s) corresponding to P09493-3 and/or P09493-1 in a sample compared to a normal control sample, comprising:
    obtaining a sample;
    contacting the sample in vitro with:
        a first antibody that binds specifically to an exon epitope of P09493-3 and P09493-1, wherein said epitope does not comprise exon 1a (SEQ ID NO:1); and
        a second antibody that binds specifically to an exon 1a (SEQ ID NO:1) epitope of P09493-3 and P09493-1, wherein the first and second antibodies are detectably labelled; and
    detecting the binding of the first and second antibodies to the exon epitope and exon 1a epitope of P09493-3 and P09493-1 and comparing the antibody binding detection results using the sample with antibody binding detection results using a control sample from subject(s) that do not have Alzheimer's Disease or Mild Cognitive Impairment.

2. A method according to claim 1, wherein the sample is a blood, or platelet sample.

3. The method of claim 1, wherein the sample is obtained from a patient.

4. The method of claim 3, wherein the patient is suspected of having Alzheimer's Disease or Mild Cognitive Impairment.

5. The method of claim 1, wherein the sample is obtained from a patient suspected of having Alzheimer's Disease or Mild Cognitive Impairment.

6. A kit comprising:
    a first probe that binds specifically to an exon epitope of P09493-3 and P09493-1, wherein said epitope does not comprise exon 1a (SEQ ID NO:1), and
    a second probe that binds specifically to an exon 1a (SEQ ID NO:1) epitope of P09493-3 and P09493-1, the first or second probes being detectably labelled with a reporter moiety.

7. A kit according to claim 6, wherein the probes are antibodies.

* * * * *

SEQUENCE LISTING

<160> NUMBER OF SEQ ID NOS: 4

<210> SEQ ID NO 1
<211> LENGTH: 20
<212> TYPE: PRT
<213> ORGANISM: Homo sapiens

<400> SEQUENCE: 1

Leu Asp Lys Glu Asn Ala Leu Asp Arg Ala Glu Gln Ala Glu Ala Asp
1               5                   10                  15

Lys Lys Ala Ala
            20

<210> SEQ ID NO 2
<211> LENGTH: 27
<212> TYPE: PRT
<213> ORGANISM: Homo sapiens

<400> SEQUENCE: 2

Glu Lys Val Ala His Ala Lys Glu Glu Asn Leu Ser Met His Gln Met

-continued

```
1               5               10              15
Leu Asp Gln Thr Leu Leu Glu Leu Asn Asn Met
            20              25

<210> SEQ ID NO 3
<211> LENGTH: 21
<212> TYPE: PRT
<213> ORGANISM: Homo sapiens

<400> SEQUENCE: 3

Cys Leu Asp Lys Glu Asn Ala Leu Asp Arg Ala Glu Gln Ala Glu Ala
1               5                   10                  15

Asp Lys Lys Ala Ala
            20

<210> SEQ ID NO 4
<211> LENGTH: 28
<212> TYPE: PRT
<213> ORGANISM: Homo sapiens

<400> SEQUENCE: 4

Cys Glu Lys Val Ala His Ala Lys Glu Glu Asn Leu Ser Met His Gln
1               5                   10                  15

Met Leu Asp Gln Thr Leu Leu Glu Leu Asn Asn Met
            20                  25
```